United States Patent [19]

Rossner

[11] Patent Number: 4,715,815
[45] Date of Patent: Dec. 29, 1987

[54] DENTAL ARTICULATOR

[76] Inventor: Hans Rossner, Ulmerstr. 11, D-8940 Memmingen, Fed. Rep. of Germany

[21] Appl. No.: 777,926

[22] Filed: Sep. 19, 1985

[30] Foreign Application Priority Data

Apr. 1, 1985 [DE] Fed. Rep. of Germany ....... 3511928

[51] Int. Cl.$^4$ .............................................. A61C 11/00
[52] U.S. Cl. ........................................ 433/60; 433/61; 433/62; 433/64
[58] Field of Search ...................... 433/60, 61, 62, 63, 433/64, 65

[56] References Cited

U.S. PATENT DOCUMENTS

| | | | |
|---|---|---|---|
| 1,271,161 | 7/1918 | Hall | 433/60 |
| 2,534,023 | 12/1950 | Hirschhorn | 433/66 |
| 3,092,909 | 6/1963 | Miller | 433/60 |
| 3,653,126 | 4/1972 | Hansen | 433/60 |
| 4,315,740 | 2/1982 | Mercer et al. | 433/63 |

FOREIGN PATENT DOCUMENTS 3003929 8/1981 Fed. Rep. of Germany ........ 433/60
3202997 7/1983 Fed. Rep. of Germany ........ 433/60

Primary Examiner—John J. Wilson
Attorney, Agent, or Firm—Peter K. Kontler

[57] ABSTRACT

A dental articulator wherein each of two pivotally joined arms carries a plate-like first support and a shallow trough-shaped second support which confines a mass of synthetic thermoplastic material serving to couple the second support to the first support. If the position of the second support relative to the first support is to be adjusted, the mass of thermoplastic material is plasticized so that such mass then acts not unlike a universal joint which enables the two supports to assume any one of an infinite number of different positions relative to each other. Each second support can carry a dental model and can be provided with a magnetic insert to attract a complementary magnet of the model.

17 Claims, 4 Drawing Figures

DENTAL ARTICULATOR

BACKGROUND OF THE INVENTION

The present invention relates to dental articulators in general, and more particularly to improvements in means for separably securing dental models to the arms of dental articulators.

Commonly owned German Pat. No. 32 02 997 discloses a dental articulator wherein each arm carries a fixedly and permanently mounted plate-like support for a detachable dental model which is made from plaster of paris or the like. That side of each support which faces away from the respective arm is provided with elongated protuberances whose height decreases in a direction from the periphery toward the center of the support and which can enter complementary grooves in the adjacent side of the corresponding dental model so that the latter can be repeatedly detached from and reattached to the support in one and the same position. The technique which is disclosed in the German patent is known as "quicksplit system" and has gained widespread acceptance by the makers of artificial dentures. Suitable magnetic means are provided to attract the base of the dental pattern to the support which is affixed to the respective arm of the articulator. The patented invention solves the problems which arise when the dental models are secured to their supports by screws. It has been found that a screw cannot be reapplied with a requisite degree of accuracy which, in the case of dentures, must be in the range of a few thousandths of one millimeter. Renewed mounting of a dental model on the arm of an articulator in one and the same position is of considerable importance for documentation purposes, for examination of dentures and/or for so-called cross mounting.

A problem which still remains to be solved is that of using two or more articulators interchangeably, i.e., of transferring a dental model from one articulator into another without any deviations of the position of the transferred model from an optimum position. This is not possible in presently known articulators due to unavoidable manufacturing tolerances. Thus, even though two or more articulators are produced by the same manufacturer in the same plant and from identical or practically identical parts, certain differences in the mounting of a dental model in two discrete articulators are observable without fail. In other words, at least some differences in the spatial position of a dental model in two discrete articulators or in mutual positions of two dental models which are transferred from a first into a second articulator are bound to exist even though the two articulators are practically identical and stem from the same source. Therefore, if a given dental model is to be reinserted in the same position as before, it is necessary to employ one and the same articulator. This entails a reduction of the utility of articulators and creates additional work because one desiring to reinstall a dental model must keep a record in order to ensure that the model will be reinserted into the articulator in which the model was installed on the previous occasion or occasions.

U.S. Pat. No. 3,092,909 discloses a method of releasably mounting dental models on dental articulators. The structure which is disclosed in this patent exhibits the drawback that its clamping device comprises a substantial number of parts and also that it does not allow for any adjustability of the plaster of paris mounts on the articulator arms with reference to the jaw models and/or vice versa.

OBJECTS AND SUMMARY OF THE INVENTION

An object of the invention is to provide a novel and improved dental articulator which is constructed and assembled in such a way that it can support any one of a small or large number of different dental models in a predetermined position irrespective of whether the model was made in the selected articulator or in another articulator.

Another object of the invention is to provide a dental articulator with novel and improved means for placing the dental models in optimum positions with reference to the arms of the articulator.

A further object of the invention is to provide novel and improved supports for use in dental articulators to carry and to allow for adjustment of dental models and the like.

An additional object of the invention is to provide novel and improved means for coupling various parts of composite supports for dental models in dental articulators.

Still another object of the invention is to provide a novel and improved method of manipulating dental models in dental articulators.

A further object of the invention is to provide a novel and improved method of converting dental articulators of one type for interchangeable use with dental articulators of another type.

Another object of the invention is to provide a dental articulator whose versatility greatly exceeds that of heretofore known dental articulators.

An additional object of the invention is to provide dental articulators which can be used interchangeably without affecting the accuracy of mounting of dental models therein and regardless of the extent to which the dimensions of such articulators deviate from optimum or standard dimensions.

A further object of the invention is to provide a dental articulator of the above outlined character wherein the primary support for a dental model can be permanently or detachably affixed to the respective arm.

The invention is embodied in a dental articulator which comprises an arm (also called bow), a first support which can constitute a metallic plate-like component, means (e.g., a threaded fastener) for fixedly securing the first support to the arm (the securing means can constitute an integral part of the arm and/or first support, i.e., the support can constitute an integral portion of the arm), a second support which can constitute a substantially trough-shaped component and serves to carry a dental model, and means for adjustably coupling the second support to the first support so that the positions of the two supports relative to each other can be changed within a desired range. The coupling means preferably comprises a universal joint, and the presently preferred coupling means comprises a mass of plastic material which is rigid within a first temperature and/or pressure range and is ductile within a second temperature and/or pressure range so that the mutual positions of the two supports can be altered when the plastic material is ductile. As mentioned above, the second support can constitute or include a shallow tray or another suitable receptacle having a bottom wall and a sidewall defining with the bottom wall a compartment or chamber for the mass of plastic material and for a portion of or the entire first support. The mass preferably contains or consists of a synthetic thermoplastic material.

The first support is preferably formed with a substantially convex front surface which faces toward the second support and is partly or fully embedded in the mass of plastic material. Such front surface preferably includes a preferably centrally located first portion and a preferably annular second portion which at least partially surrounds the first portion. The preferably flat rear surface of the first support is nearer to the second than to the first portion of the front surface.

The front surface of the second support (namely the surface which faces away from the first support) can be provided with a socket for a magnetic insert, e.g., a substantially plate-like magnet which can attract a second magnet or a feromagnetic material in the dental model. The front surface of the second support can be further provided with locating and centering means for dental models, e.g., one or more female detent elements in the form of recesses or grooves extending substantially radially from the aforementioned socket in the front surface of the second support.

The novel features which are considered as characteristic of the invention are set forth in particular in the appended claims. The improved dental articulator itself, however, both as to its construction and the mode of assembling the same, together with additional features and advantages thereof, will be best understood upon perusal of the following detailed description of certain specific embodiments with reference to the accompanying drawing.

DESCRIPTION OF THE PREFERRED EMBODIMENTS

Figure 4:
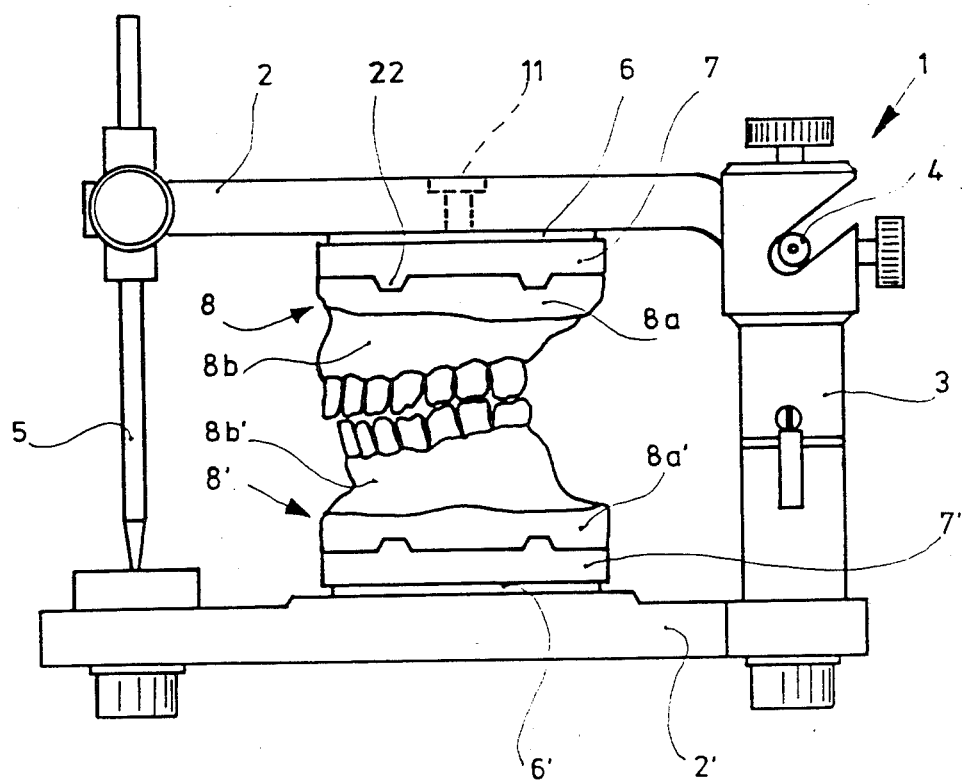
FIG. 4 is a side elevational view of an articulator with two pairs of supports of the type shown in FIGS. 1 and 2.

Referring first to FIG. 4, there is shown a dental articulator 1 which comprises two arms or bows 2, 2', a column 3 which is rigid with the arm 2, a shaft 4 which pivotably connects the column 3 with the arm 2, a customary incisal guide pin 5 which determines the extent to which the arms 2 and 2' can be pivoted toward each other, a pair of plate-like first supports 6, 6' which are fixedly and preferably (but not necessarily) detachably secured to the respective arms 2, 2', and two trough-shaped second supports 7, 7' which are respectively adjacent to the supports 6, 6' and serve to carry detachable dental models 8, 8'.

Figure 1:
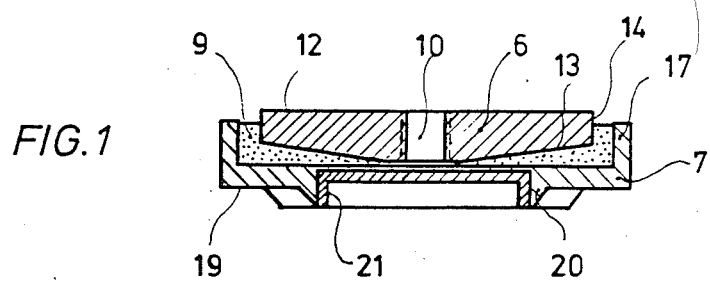
FIG. 1 is a central sectional view of a portion of a dental articulator which embodies the invention.

FIG. 1 shows the supports 6, 7 and a novel and improved coupling 9 which is used to adjustably connect the two supports to each other so that the support 7 can assume an infinite number of different positions with reference to the support 6 and/or vice versa. The central portion of the substantially circular disc- or plate-like support 6 has a tapped bore 10 which can receive the shank of a screw 11 (FIG. 4) serving to fixedly connect the support 6 to the arm 2 of the articulator 1. The rear side or surface 12 of the support 6 is flat, and its front side or surface 13 is substantially convex, i.e., its first or central portion (in the region of the bore 10) is more distant from the rear surface 12 than the annular second portion which surrounds the first portion and extends all the way to the peripheral surface 14 of the support 6. The bore 10 and the screw 11 can be omitted if the means for fixedly connecting the support 6 to the arm 2 includes an integral portion of the arm 2 and/or support 6, i.e., if the components 2 and 6 are made of a single piece of suitable metallic material or are welded or otherwise permanently bonded to each other. The provision of a bore 10 and the utilization of a screw 11 or a similar fastener are preferred if the support 6 is to be fixedly secured to one arm of the skeleton of an existing conventional dental articulator.

The coupling 9 is preferably a mass of synthetic thermoplastic material which is ductile (i.e., capable of being fashioned into a new form) within a first range of temperatures but is hard within a second range of temperatures. Thus, all that is necessary to change the orientation of the support 7 relative to the support 6 and/or vice versa is to raise the temperature of the mass which constitutes the coupling 9 to a temperature at which the mass is pliant and permits a desired adjustment of the supports 6 and 7 relative to each other. The mass adheres to the two supports so that such supports are fixedly held against any displacement relative to each other as soon as the temperature of the plastic material is reduced sufficiently to cause a setting and retention of the supports 6 and 7 in their selected mutual positions.

It is necessary to apply a pronounced force if one desires to separate the supports 6 and 7 from each other by destroying the mass of plastic material which constitutes the coupling 9 or by causing a separation of such mass from the support 6 and/or 7 while the temperature of the mass is within the second range.

The rear surface 12 of the support 6 need not be flat. All that counts is to ensure that this surface preferably conforms to the adjacent surface of the arm 2 when the parts 2 and 6 are fixedly connected to each other. In order to ensure that the support 6 can be repeatedly fixed to the arm 2 in one and the same angular position, the rear surface 12 is formed with one or more notches 15 which are spaced apart from the bore 10 and can receive complementary protuberances (not specifically shown) at the underside of the arm 2. If desired, the central portion of the front surface 13 of the support 6 can be flat and the annular second portion of the front surface 13 is then slightly conical or substantially conical so as to guarantee that the thickness of the support 6 decreases, preferably gradually, in a direction from the bore 10 toward the peripheral surface 14. The support 6 can be said to resemble a lentil with one of its sides flattened to conform to the outline of the adjacent portion of the arm 2. Such configuration of the support 6 renders it possible to further increase the number of different positions which the supports 6 and 7 can assume relative to each other, especially to increase the extent to which the supports 6 and 7 can be tilted relative to each other provided, of course, that the mass which forms the coupling 9 is then maintained at a temperature at which the plastic material is ductile.

The support 7 is a rather shallow receptacle in the form of a substantially circular trough with a bottom wall 16 and a peripheral wall or sidewall 17 which extends from the rear side of the bottom wall and defines therewith a shallow compartment 18 for the mass of the coupling 9 as well as for a portion of or the entire support 6.

The illustrated supports 6 and 7 have substantially circular shapes; however, it is equally within the purview of the invention to employ polygonal, oval or otherwise configurated supports. The diameter of the peripheral surface 14 of the support 6 is somewhat less than the inner diameter of the sidewall 17 so as to allow for at least some lateral shifting of the supports 6 and 7 relative to each other when the plastic material of the coupling 9 is ductile.

The front side or surface 19 of the support 7 has a centrally located ring-shaped socket 20 for a magnetic insert 21 which can attract a complementary insert (not specifically shown) in the corresponding dental model 8. In the embodiment which is shown in the drawing, the insert 21 includes or constitutes a substantially plate-like magnet with a rim which is adjacent to the internal surface of the socket 20.

Figure 2:
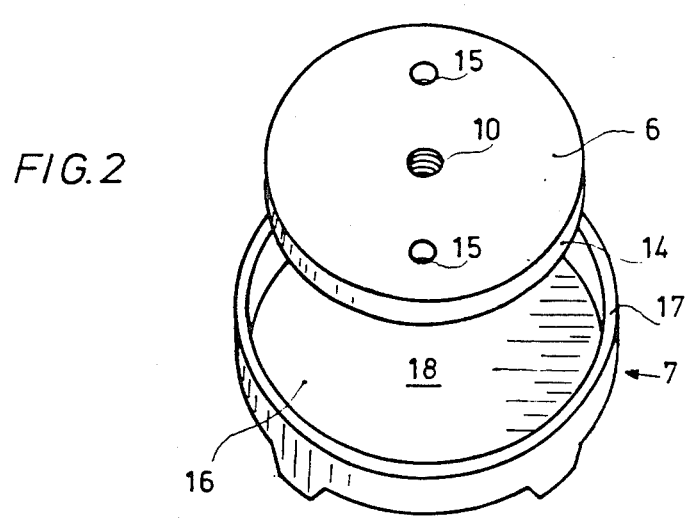
FIG. 2 is an exploded perspective view of two cooperating first and second supports which constitute component parts of the improved articulator.
Figure 3:
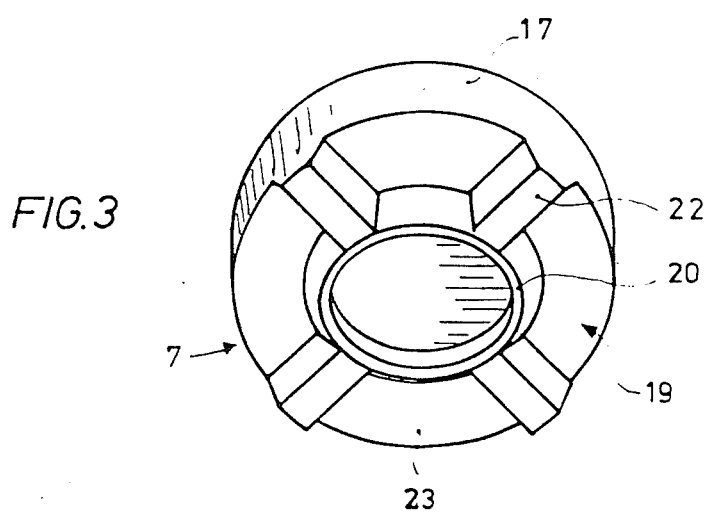
FIG. 3 is a perspective view of the second support showing the centrally located socket and the detent elements in its front surface.

The front surface 19 of the support 7 is further formed with locating means in the form of substantially radially extending alternating male and female detent elements 22 and 23 which surround the socket 20 and cooperate with complementary female and male detent elements in the adjacent side of the dental model 8 when the latter is secured to the support 7. Each detent element 22 can resemble an elongated tooth with a flat top land and two mutually inclined flanks (see particularly FIG. 2). The insert 21 can consist of steel and attracts the magnetic or magnetizable insert of the model 8 so that the latter is securely held on the support 7. Proper angular positioning of the support 7 and of the corresponding model 8 relative to each other is ensured by the detent elements 22, 23 and the complementary detent elements of the model. The manner in which the models 8 and 8' are formed and provided with replicas of the jaws forms no part of the invention. The support 7 can carry any one of a wide variety of differently shaped models 8.

The supports 6 and 7 preferably consist of a nonmagnetic material, such as aluminum. This is in contrast to the teaching of the aforesaid German patent which proposes to make the supports on the arms of the articulator of a magnetizable material, such as steel.

The manner in which the support 7' is coupled to and adjustable relative to the support 6' is the same as described above with reference to the arm 2 and supports 6, 7. The support 6' is assumed to be integral with the arm 2'.

An important advantage of the improved dental articulator is its pronounced versatility. Thus, the combination of supports 6, 7 and/or 6', 7' can be utilized in dental articulators wherein the first supports 6 and 6' are integrally (non-separably) connected to the respective arms of the skeleton frame of the articulator as well as in articulators of the type wherein the first supports 6 and 6' can be repeatedly detached from and reattached to the respective arms. The improved couplings between the supports 6, 7 and 6', 7' render it possible to repeatedly mount the supports 7 and 7' on the associated supports 6 and 6' in one and the same position without any deviation whatever between a position prior to and a position subsequent to detachment from (and subsequent reattachment to) the associated first support. In other words, a dental technician or a dental laboratory need not maintain a single type of dental articulators but can utilize the improved combinations of first and second supports irrespective of the basic design of the articulators, i.e., regardless of whether the first supports are permanently or separably affixed to the corresponding arms. The universal adjustability of the supports 7, 7' relative to the associated supports 6, 6' renders it possible to ensure that the antagonistic points of two models 8, 8' which are transferred from a first into a second articulator are held in identical positions with reference to each other and that such identical positioning of antagonistic points can be repeated as often as desired, in one and the same articulator or in different articulators. Moreover, the improved combinations of first and second supports (with the improved coupling means 9 therebetween) obviate the need to manufacture the skeleton frames of dental articulators with a very high degree of precision because any deviations from the standard configuration and/or dimensions of the skeleton frame can be compensated for by universal adjustability of the second supports relative to the associated first supports. Unavoidable manufacturing tolerances render it impossible to ensure the making of a short or long series of identical dental articulators, and the novel combination of first and second supports solves this problem in a simple and efficient way by rendering it possible to alter the position of the second support relative to the first support until the selected position of the second support coincides with an optimum position or matches, exactly, the previously selected position.

A further important advantage of the improved dental articulator is that it can be obtained by conversion of conventional articulators. Thus, and as already explained above, if a conventional articulator comprises two supports which are fixedly secured to the respective arms, each such support can be associated with a support 7 or 7' and the support 7 or 7' can be adjustably secured to the fixedly mounted support by a mass of plastic material which performs the function of a universal joint as soon as it is caused or permitted to become ductile. If a conventional dental articulator comprises a pair of detachable plate-like supports which are threadedly or otherwise (separably) connected to the respective arms, the conversion into an articulator which embodies the present invention is just as simple or even simpler, i.e., such articulator is again provided with at least one second support which is coupled to the selected detachably mounted support by a mass of plastic material which can be caused to become ductile and to thus allow for practically universal adjustment of the second support relative to the associated first support. At the present time, and if the invention is to be embodied in an articulator which is about to be manufactured, the support 6 and/or 6' is preferably integral with the respective arm 2 or 2' for the sake of simplicity, lower cost and a reduction in the overall number of parts. All that counts is to ensure that the support 6 or 6' can be fixedly secured to or made integral with the respective arm 2 or 2' so as to make sure that no changes in orientation of the composite support 6, 7 or 6', 7' are possible after the position of the support 7 or 7' with reference to the associated support 6 or 6' is already selected (while the plastic mass is ductile) and thereupon fixed (by permitting the plastic material to set) while the support 7 or 7' is held in the selected position.

The utilization of magnetic means for separably connecting the second support with the corresponding model is particularly desirable and advantageous in connection with the supports 7, i.e., with supports which are to carry the models of the upper jaws.

If the basic design of a dental articulator is identical with or resembles that of the articulator which is disclosed in the aforediscussed commonly owned German Pat. No. 32 02 997, and if such dental articulator is to be used interchangeably with articulators of the type shown in FIG. 4, one can proceed as follows:

The patented articulator (hereinafter called master) is used to make a so-called adjusting base or pattern which is assembled of two secondary bases connected to each other by plaster of paris to constitute a one-piece body. The pattern is used to connect the mounting plate on the upper arm with the mounting plate on the lower arm of the master. One arm of the articulator of the present invention (hereinafter called improved articulator) which is to be adjusted in dependency on the master carries the novel combination of first and second supports, and the other arm of the improved articulator carries an assembly of parts which is the same as the assembly on one arm of the master. The pattern is placed between the novel combination of supports on one arm and the conventional assembly of parts on the other arm of the improved articulator. If the orientation of the pattern in the improved articulator deviates from the orientation in the master, the plastic material of the coupling 9 is heated to allow for universal adjustment of the support 7 relative to the support 6 until the orientation of the pattern in the improved articulator matches the orientation of the pattern in the master. Thus, the invention can be embodied in dental articulators which exhibit the features of the patented articulator (master) as well as the features of the present invention. The dental model which is carried by the support 7 or 7' shares all movements of such support relative to the associated support 6 or 6' because the insert 21 cooperates with the magnet or magnetizable component of the dental model to ensure that each change of orientation of the support 7 or 7' entails an identical change in orientation of the associated dental model 8 or 8'. The change in orientation can involve a movement of the support 7 or 7' and the associated model 8 or 8' from a position in which the axis of the support 7 or 7' coincides with the axis of the associated support 6 or 6' to a position in which the axes of the supports 6, 7 or 6', 7' make a relatively small or a relatively large acute angle, or vice versa. The support 7 or 7' is prevented from changing its position relative to the support 6 or 6' as soon as the plastic material of the respective coupling 9 is caused or allowed to set.

Once the support 7 or 7' of the improved articulator is fixed in its selected position with reference to the support 6 or 6', the master and the improved articulator can be used interchangeably even though the master does not embody any of the features of the present invention and the improved articulator employs only a single pair of supports 6, 7 or 6', 7'. In other words, a dental model which was held first in the master can thereafter be mounted in the improved articulator with the same degree of accuracy, and vice versa.

It is presently preferred to mass produce the supports 6, 6' and especially the supports 7, 7' in the form of a long series of identical parts which, as stated above, can be made of aluminum or another nonmagnetic material. At the very least, the supports of each series should be sufficiently similar to ensure that any of the supports 6 or 6' can be used with any of the supports 7 or 7' without appreciably affecting the extent to which the associated supports 6, 7 or 6', 7' are adjustable relative to each other.

In order to simplify the making of the models 8 and 8', each of these models can comprise a plaster of paris base ($8a$, $8a'$) which carries the respective replica ($8b$, $8b'$) of the jaw. The magnet or magnetizable insert which cooperates with the insert 21 of the respective support 7, 7' is incorporated in the corresponding base $8a$, $8a'$. If desired, the entire support 7 or 7' can be made of steel or another magnetic material so that the corresponding insert 21 can be dispensed with. It is necessary to ensure that the attraction between the supports 7, 7' and the respective bases $8a$, $8a'$ will suffice to prevent accidental separation of the bases but that the bases can be detached in response to the application of a force which overcomes the magnetically induced attraction between the parts 7, 7' on the one hand and the parts $8a$, $8a'$ on the other hand. The bases $8a$ and $8b$ can be provided with sockets for extractible permanent magnets which cooperate with the inserts 21 of the supports 7, 7' or directly with the supports 7, 7' if the latter are made of steel or the like. Removal of permanent magnets from the sockets of the bases $8a$, $8a'$ is desirable and advantageous because this renders it possible to operate in accordance with the so-called control base technique. The male and female detent elements 22, 23 render it possible to repeatedly attach the bases $8a$, $8a'$ to the respective supports 7, 7' in the same positions as before. The male detent elements 22 of the supports 7, 7' can enter complementary female detent elements of the adjacent bases $8a$, $8a'$ with a high degree of accuracy and reproducibility because the material of the supports 7, 7' is preferably a metal. This ensures highly predictable reattachment of the bases to the respective second supports. The configuration of each of the male detent elements 22 can deviate from the illustrated configuration without departing from the spirit of the invention. For example, the front surface of each of the supports 7, 7' can be provided with a plurality of pyramidal, conical and/or otherwise configurated male detent elements as long as they can readily penetrate into and can be readily extracted from the corresponding female detent elements. The front surfaces of the supports 7, 7' are or can be finished with a high degree of precision so as to further enhance the accuracy of reattachment of the bases $8a$ and $8a'$ to the respective second supports.

The presently preferred plastic materials of the mass which constitutes the coupling 9 include natural and synthetic waxes and wax mixtures as well as vinyls, polystyrenes, polyethylene, polyesters and polyamides which preferably have a melting point of not less than 70° C. (158° F.).

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A dental articulator comprising an arm; a first support on said arm; a second support arranged to carry a dental model; and means for adjustably coupling said second support to said first support, comprising a mass of plastic material which is rigid a first temperature range and is ductile within a second temperature range so that the mutual positions of said supports can be repeatedly altered by rendering the plastic material ductile, said second support including a receptacle having a bottom wall and a sidewall defining with the bottom wall a compartment containing the mass of plastic material, at least a portion of said first support being at least partially embedded in said mass within said compartment.

2. The articulator of claim 1, wherein said receptacle is a shallow trough.

3. The articulator of claim 1, wherein said first support has a substantially convex front surface facing said second support.

4. The articulator of claim 3, wherein said front surface includes a first portion and a second portion at least partially surrounding said first portion, said first support further having a rear surface facing away from said second support and the first portion of said front surface being more distant from said rear surface than said second portion.

5. The articulator of claim 1, wherein said mass contains a synthetic thermoplastic material.

6. The articulator of claim 1, wherein said second support has a front surface facing away from said first support and a socket in said front surface, and further comprising a magnetic insert in said socket.

7. The articulator of claim 6, wherein said insert includes a substantially plate-like magnet.

8. The articulator of claim 1, wherein said second support has a front surface facing away from said first support and provided with locating means for dental models.

9. The articulator of claim 8, wherein said locating means includes at least one female detent element in said front surface.

10. The articulator of claim 1, further comprising means for fixedly securing said first support to said arm.

11. The articulator of claim 1, wherein said first support is integral with said arm.

12. The articulator of claim 1, further comprising a second arm which is movable with reference to said first mentioned arm, an additional first support on said second arm, an additional second support arranged to carry a second dental model, and means for adjustably coupling said additional second support to said additional first support.

13. The articulator of claim 12, wherein said means for adjustably coupling said additional second support to said additional first support comprises a mass of plastic material which is rigid within a first temperature range and is ductile within a second temperature range so that the mutual positions of said additional supports can be altered when the plastic material is ductile.

14. The articulator of claim 1, wherein at least one of said supports consists of a metallic material.

15. The articulator of claim 1, wherein at least one of said supports consists of aluminum.

16. The articulator of claim 1, wherein at least one of said supports has a substantially circular shape.

17. The articulator of claim 1, wherein said plastic material is selected from the group consisting of natural and synthetic waxes and wax mixtures, vinyls, polystyrenes, polyethylene, polyesters and polyamides.

* * * * *